United States Patent [19]

Kung et al.

[11] Patent Number: 4,777,319

[45] Date of Patent: Oct. 11, 1988

[54] OXIDATIVE DEHYDROGENATION OF ALKANES TO UNSATURATED HYDROCARBONS

[75] Inventors: Harold H. Kung, Wilmette, Ill.; Mohamed A. Chaar, Homs, Syria

[73] Assignee: Northwestern University, Evanston, Ill.

[21] Appl. No.: 69,284

[22] Filed: Jul. 1, 1987

[51] Int. Cl.$^4$ .................... C07C 5/09; C07C 5/327
[52] U.S. Cl. ................................. 585/624; 585/443; 585/658
[58] Field of Search .................. 585/443, 624, 658

[56] References Cited

U.S. PATENT DOCUMENTS

| | | | |
|---|---|---|---|
| 4,250,346 | 2/1981 | Young et al. | 585/658 |
| 4,524,236 | 6/1985 | McCain | 585/658 |
| 4,568,790 | 2/1986 | McCain | 585/658 |
| 4,596,787 | 6/1986 | Manyik et al. | 585/658 |
| 4,727,208 | 2/1988 | King | 585/428 |

*Primary Examiner*—Curtis R. Davis
*Attorney, Agent, or Firm*—Tilton, Fallon, Lungmus & Chestnut

[57] ABSTRACT

Oxidative dehydrogenation of alkanes to unsaturated hydrocarbons is carried out over metal vanadate catalysts under oxidizing conditions. The vanadate catalysts are represented by the formulas $M_3(VO_4)_2$ and $MV_2O_6$, M representing Mg, Zn, Ca, Pb, or Cd. The reaction is carried out in the presence of oxygen, but the formation of oxygenate by-products is suppressed.

24 Claims, No Drawings

OXIDATIVE DEHYDROGENATION OF ALKANES TO UNSATURATED HYDROCARBONS

GRANT REFERENCE

Research leading to this invention was supported in part by a grant from the United States Department of Energy, Grant No. DE-AC02-78ER4987. The U.S. Government has rights therein.

FIELD OF INVENTION

The field of this invention is the catalytic dehydrogenation of alkanes. The invention is particularly concerned with the selective oxidative dehydrogenation of shortchain hydrocarbons to produce unsaturated hydrocarbons.

BACKGROUND OF INVENTION

There have been few reports on the use of oxygen to achieve high selectivity in the oxidative dehydrogenation of alkanes. Alkanes are generally much less reactive than the dehydrogenation products, such as alkenes, dienes, or aromatics. Because of the high temperatures required to activate alkanes, their dehydrogenated products react rapidly with oxygen to form combustion products. Production of useful products by oxidative dehydrogenation of alkanes has therefore usually been limited to the production of oxidized derivatives, viz. aldehydes or organic acids.

Metal oxides have been used as catalysts for dehydrogenation of hydrocarbons. Magnesium oxide is known to be selective for dehydrogenation but its activity is very low for this purpose. Stepanov, et al. (1981). On the other hand, vanadium oxide is active for the oxidation of butane, but its selectivity is only about 10%. Mori, et al. (1983); and Bretton, et al. (1952).

Magnesium vanadale (V-Mg-O) catalysts have been tested for a few oxidative dehydrogenation reactions. A V-Mg-O catalyst was found to be selective for the conversion of ethyl benzene to styrene. Oganowski, et al. (1984); and Hanuza, et al. (1985). This catalyst was also found to be selective for conversion of butene to butadiene. Simakov, et al. (1985). The active compound was identified by Hanuza et al. (1985) as magnesium orthovanadate; $MG_3(VO_4)_2$.

As far as is known, there have been no reports on the use of magnesium orthovanadate or other V-Mg-O catalysts for dehydrogenation of alkanes. Similarly, no such references are known for the corresponding V-Zn-O catalysts. Certain other metal oxide catalysts have been shown to exhibit some selectivity for conversion of alkanes to unsaturated hydrocarbons, viz. Mg-Mo-O, Ni-Mo-O, and Co-Mo-O catalysts. See Stepanov, et al. (1981); and Doroschenko, et al. (1982). It has also been found that V-P-O catalyzes the oxidation of butane to maleic anhydride. Hodnett (1985).

The selective oxidative dehydrogenation of alkanes has remained a challenging problem. Under conditions which activate the alkanes, reactions may be expected to proceed to oxygenated products such as aldehydes or organic acids, and/or to the partial or complete combustion, forming CO or $CO_2$. These considerations have probably operated as counter-incentives to research on the production of unsaturated hydrocarbons from alkanes.

SUMMARY OF INVENTION

This invention is based on the discovery that a class of metal vanadate catalysts is highly selective for the conversion of $C_3$ to $C_6$ saturated aliphatic hydrocarbons to unsaturated products. Not only are these metal vanadate catalysts highly selective but good conversions can be obtained. The formation of oxygenate by-products (e.g., aldehydes and acids) is essentially suppressed. Catalytically effective ratios of oxygen to alkane can be employed at sufficiently high temperatures to promote the desired dehydrogenation reactions. It is surprising that only negligible amounts of aldehydes and organic acids are produced.

The general class of selective vanadate catalysts for use in the method of this invention can be represented by the formulas $M_3(VO_4)_2$ and $MV_2O_6$. M is preferably magnesium (Mg), zinc (Zn), or other divalent metal of similar properties. For example, the catalyst may be magnesium or zinc orthovanadate, or magnesium or zinc metavanadate. Distinctive of the class of metal vanadate catalysts is that they have similar crystal structures and are free of active oxygens such as particularly V=O groups, which shows a characteristic infrared stretching band at around 1000 to 1022 $cm^{-1}$, and a Raman band at around 960 to 987 $cm^{-1}$.

It is also believed that the class of catalysts of this invention adsorb short-chain unsaturated hydrocarbons or aromatics very weakly. The resulting surface residence time of the unsaturated hydrocarbons on the catalyst probably decreases the chance for further oxidation to aldehydes or acids.

DETAILED DESCRIPTION

One preferred sub-group of catalysts for use in the method of this invention is the orthovanadates represented by the formula $M_3(VO_4)_2$ wherein M preferably is magesium or zinc. Other bivalent metals can be substituted which will replace the magnesium or zinc in the crystal lattice of the vanadate. These include calcium, lead, and cadmium.

Alternatively, metavanadate catalysts can be employed having the general formula $MV_2O_6$. M preferably designates magnesium or zinc, but other metals may replace the magnesium or zinc in the metavanadate crystal structure. For example, with respect to both $M_3(VO_4)_2$ and $MV_2O_6$ catalysts, in general, lead, cadmium, and calcium can partially or wholly replace magnesium or zinc while producing similar crystalline materials.

Specific representative catalyst compounds include:
(1) $MG_3(VO_4)_2$
(2) $Zn_3(VO_4)_2$
(3) $MgV_2O_6$
(4) $ZnV_2O_6$ Magnesium or zinc orthovanadate or metavanadate need not be purely Mg or Zn crystals. The Mg and Zn may be used in an intermixed form, the crystalline structure containing varying proportions of magnesium, zinc, or other substitutable metal. For example, the class of such mixed Mg/Zn crystals can be represented by the formulas:
(5) $Mg_{3-x}Zn_x(VO_4)_2$, and
(6) $Mg_{1-x}Zn_xV_2O_6$.

Characteristic of the class of catalysts usable with the method of this invention is that they are free of active oxygen as represented by the group, V=O. This group possesses a characteristic infrared stretching frequency at 1022 cm$^{-1}$, and a Raman band at 987 cm$^{-1}$. See Inomata, et al. (1981); Iwamoto, et al. (1985); and Mori, et al. (1986). A similar IR band around 1000 cm$^{-1}$ and a Raman band around 960 cm$^{-1}$ are also present on V-P-O, indicating the presence of V=O groups. Moser, et al. (1985). As distinguished from V$_2$O$_5$ and V-P-O, the crystalline orthovanadates and metavanadates are free from V=O. The crystal structure is believed to be important for the desired result of suppressing oxygenate by-product formation. Freedom from V=O and probable weak surface adsorption of the products make possible the selective conversion of alkanes to unsaturated hydrocarbons.

The catalyst compounds of this invention can be readily prepared by known processes, or purchased from commercial sources, if available. For example, magnesium metavanadate is supplied by Strem Chemicals, Inc., Newburyport, Massachusetts.

In one method of preparation, MgO or ZnO are first prepared. They may be formed by precipitation from an aqueous solution of magnesium and/or zinc nitrate, using ammonium carbonate at a neutral pH (6.5 to 7.0). The metal oxide precipitate is dried, calcined, and ground to a fine powder. The MgO or ZnO powder may be added to an aqueous solution of ammonium vanadate/ammonium hydroxide. In place of MgO or ZnO, other Mg or Zn compounds may be used, such as magnesium or zinc carbonate, magnesium hydroxide, zinc hydroxycarbonate, or oxalates. The solution can be evaporated to dryness to obtain a solid material which is calcined to form magnesium and/or zinc orthovanadate. For example, calcining at around 550° C. for six hours is sufficient. The resulting solid may then be crushed to form the catalyst material.

Literature references describing preparation of metal orthovanadates include Clark, et al. (1976).

Magnesium or zinc metavanadates may be prepared as follows: MgO or ZnO powder may be well mixed with V$_2$O$_5$ powder or solid ammonium vanadate. The mixture is calcined to form magnesium or zinc metavanadate. Literature citations illustrating the preparation of corresponding metal vanadates are Clark, et al. (1976), Kristallov, et al. (1984).

If desired, the active catalysts of this invention may be applied to catalyst supports. However, they can also be used as essentially pure compounds in a finely-divided particulate form. Particulate sizes of $-100$ mesh (American Standard Screen) may be used. The catalyst particles may be employed in either a stationary or a fluidized bed. Standard procedures for contacting a reaction mixture with solid catalyst materials in porous beds can be used. The catalyst is formed into the porous bed, and the vapor phase reaction mixture is passed therethrough, with or without fluidization of the bed.

The gas phase reaction mixture will include the saturated hydrocarbon reactant and the oxygen. An inert carrier gas can be employed, such as nitrogen, helium, etc. Air may be employed as the source of oxygen, and also to provide the nitrogen carrier gas, providing the desired molar ratio of oxygen to alkane is obtained. If needed, additional nitrogen or oxygen can be added to adjust the alkane/O$_2$ ratio.

The oxidative dehydrogenation method of this invention can utilize reaction mixtures containing from 0.5 to 10 moles of oxygen (O$_2$) per mole of alkane. In preferred embodiments, however, the moles of oxygen are limited to 4 moles O$_2$/ mole alkane. Typical preferred ratios are from 0.5 to 3.0 moles O$_2$ per mole alkane. For example, a 1:1 or 2:1 ratio of O$_2$ to alkane is desirable.

The temperatures required to promote the reaction are generally in the range from 300° to 700° C. Temperature is not highly critical. Usually, temperatures from about 400° C. to 600° C. are satisfactory. Given the oxygen to alkane ratios described, and utilizing temperatures as described, good conversions of alkanes to unsaturated hydrocarbons can be obtained while at the same time avoiding the formation of oxygenated hydrocarbon by-products. Some CO and/or CO$_2$ will be produced.

The method of this invention is applicable to the class of saturated alkane reactants containing from 2 to 8 carbons. Preferred embodiments are alkane reactants containing from 3 to 6 carbons. The alkanes may be either straight or branched chain. Depending on the alkane selected, a single unsaturated hydrocarbon may be produced, or a mixture of unsaturated hydrocarbons. For example, propane can be converted to propene or a mixture of propene and ethene without the formation of acrolein. Butane can be converted to a mixture of unsaturated hydrocarbons, including butene and butadiene. Isobutane can be converted to isobutene. Pentane and hexane can be converted to mixtures of unsaturated hydrocarbons. Products from pentane may contain a mixture of pentenes and pentadienes. Products from hexane may contain a mixture of hexenes and hexadienes.

The method of this invention is further illustrated by the following examples.

EXAMPLE I

MgO was prepared by precipitation from a magnesium nitrate solution with ammonium carbonate. The pH of the solution was kept at 6.5–7.0. The precipitate was suction-filtered, washed with doubly distilled water four to five times, air dried at 80° C. or 24 h. and then calcined in air at 700° C. for 3 h. The resultant white solid was ground into a fine powder.

An appropriate amount of MgO powder was added to an aqueous solution containing 0.5 wt % ammonium vanadate and 1 wt % ammonium hydroxide at 70° C. With stirring, the suspension was evaporated to dryness. The resulting solid was calcined at 550° C. for 6 h. This solid was lightly crushed to break up the crumbs and used as a catalyst. The BET areas were determined by nitrogen adsorption spectroscopy. The compositions were determined by atomic absorption spectroscopy after the catalysts were dissolved in 0.1 M nitric acid. The reaction was carried out in a conventional flow system with a quartz U-tube reactor at close to atmospheric pressure.

Under the standard condition, the fedd was 4 vol % butane, 4 to 8% oxygen, and the balance He. The flow rate was about 100 ml/min. and the reaction temperature was 480° to 600° C. The catalyst was supported by quartz wool. Unless specified, the catalyst was mixed with twice the weight of silica (<70 mesh, Davison 62). Normally, 0.1 to 0.3 g of catalyst was used. The empty reactor showed no activity, and the results were very similar with and without the use of silica diluent. In a typical reaction run, the reactor was heated to the desired temperature in the flow of reactants. The system was allowed to stabilize for about 1 h at the reaction temperature before the first product analysis was made. A typical run lasted for about 3 h. No deactivation of the catalyst was observed, and the catalyst could be reused without additional treatment.

The reaction products were analyzed by on-line gas chromatography. A gas chromatograph equipped with a thermal conductivity detector was used. Helium was the carrier gas.

RESULTS

Catalyst Characterization

Table 1 lists the compositions and the surface areas of the catalysts used. The number in the catalyst label denotes the approximate weight percentage of $V_2O_5$ As prepared, the color of the catalyst ranged from white for MgO and for those of low vanadium content, to slightly yellow for those of high vanadium content. The color of the catalysts did not change after reaction studies.

Results of X-ray diffraction are shown in Table 2. Up to a vanadium content of 24 wt %, only MgO diffraction lines were detected. As this composition, if all the vanadium in the catalyst reacted with MgO to form magnesium orthovanadate, $Mg_3(VO_4)_2$, the catalyst would contain about 8 mol % orthovanadate. This corresponded roughly to the detection limit of the X-ray diffraction technique used. In samples containing a higher vanadium content, diffraction lines of MgO and magnesium orthovanadate were detected. Other possible compounds of V-Mg-O, such as $MgV_2O_6$ and $Mg_2V_2O_7$, were not detected. For the 54 V-Mg-O sample, a diffraction line that corresponded to a d spacing of 1.51 Å was detected. $V_2O_5$ had a diffraction line at this position. However, the more intense lines for $V_2O_5$ at 4.38 and 3.40 Å were not detected. Thus the assignment of this line to $V_2O_5$ was in doubt.

TABLE 1

Compositions and Surface Areas of the Catalysts.

| Catalyst | Surface Area $M^2/g$ | Wt % MgO | Wt % $V_2O_5$ | Mole % MgO | Mole % $V_2O_5$ |
|---|---|---|---|---|---|
| MgO | 28 | 100 | 0 | 100 | 0 |
| $V_2O_5$ | 3.5 | 0 | 100 | 0 | 100 |
| 3V—Mg—O | 82 | 96.5 | 3.5 | 99.2 | 0.8 |
| 8V—Mg—O | 91 | 92.1 | 7.9 | 98.1 | 1.9 |
| 19V—Mg—O | 46[a] | 81.1 | 18.9 | 9S.1 | 4.9 |
| 24V—Mg—O | 74 | 76.3 | 23.7 | 93.6 | 6.4 |
| 35V—Mg—O | 51 | 64.9 | 35.1 | 89.3 | 10.7 |
| 54V—Mg—O | 49 | 46.3 | 53.6 | 79.6 | 20.4 |

[a] value for a used catalyst

TABLE 2

X-ray Diffraction Lines from V—Mg—O and Their Assignments d-spacing, A (relative intensity)

| 8V—Mg—O | 19V—Mg—O | 24V—Mg—O | 35V—Mg—O | 54V—Mg—O | Assignments[a] |
|---|---|---|---|---|---|
| | | | | 3.29(22) | $Mg_3V_2O_8$ |
| | | | 3.03(7) | 3.02(34) | $Mg_3V_2O_8$ |
| | | | 2.87(5) | 2.86(23) | $Mg_3V_2O_8$ |
| | | | 2.54(22) | 2.55(100) | $Mg_3V_2O_8$ |
| | | | 2.49(7) | 2.49(44) | $Mg_3V_2O_8$ |
| 2.43(6) | 2.42(4) | 2.43(6) | | | MgO |
| 2.10(100) | 2.10(100) | 2.10(100) | 2.10(100) | 2.10(61)[b] | MgO |
| | | | | 2.08(71) | $Mg_3V_2O_8$ |
| | | | 1.71(2) | 1.71(10) | $Mg_3V_2O_8$ |
| | | | 1.58(3) | 1.58(13) | $Mg_3V_2O_8$ |
| | | | | 1.51(23) | $V_2O_5$ (?) |
| 1.49(57) | 1.49(53) | 1.49(53) | 1.49(60) | 1.49(46) | MgO |
| | | | | 1.47(68) | $Mg_3V_2O_8$ |
| | | | | 1.43(10) | $Mg_3V_2O_8$ |
| 1.269(5) | 1.269(5) | 1.270(5) | 1.27(3) | | MgO |
| 1.216(13) | 1.218(12) | 1.215(11) | 1.22(10) | | MgO |
| 1.053(5) | 1.053(5) | 1.052(5) | | | MgO |
| | | | | 1.04(7) | $Mg_3V_2O_8$ |
| 0.966(2) | 0.966(3) | | | | MgO |
| 0.942(13) | 0.943(12) | | 0.94(16) | | MgO |

Footnote
[a] Made according to the published diffraction patterns, Joint Committee For Powder Diffraction Standards, Swarthmore, PA, Powder diffraction file card no. 9-387 ($V_2O_5$), 23-1233 ($MgV_2O_6$), 29-877 ($Mg_2V_2O_7$), 19-779 ($Mg_3V_2O_8$), and 4-829 (MgO). For $Mg_3V_2O_8$, the data of A. Durif, Anal. Chem., 31, 1741 (1959) was also used.
[b] a broad peak

Reaction Study

The catalysts containing vanadium are generally very active beginning at about 500° C. Oxidative dehydrogenation and combustion are the major reactions. Table 3 shows the reaction products from the various catalysts at 540° C. On the V-Mg-O catalysts, 1-butene, cis- and trans-2-butene, butadiene, CO, and $CO_2$ are always the major products. Small amounts of ethane and ethene (which were not separated) and propane and propene were also observed. Since the carbon balance based on the products listed was satisfied in all runs to within ±5%, no attempt was made to collect any condensable products.

As shown in Table 3 unsupported vanadium oxide showed low activity and low selectivity for oxidative dehydrogenation. The selectivity was low even at low conversions, and the dehydrogenation product was 1-butene. Interestingly, a much higher selectivity to $C_3$ products was observed at low conversion than at high conversion. A small amount of butadiene was also produced at high conversion. For MgO, the activity and the dehydrogenation selectivity were also low, and the dehydrogenation products were also butenes. A substantial selectivity for the cracked products was also observed.

TABLE 3

Conversion and Selectivity in Butane Oxidative Dehydrogenation over V—Mg—O[a]

| Catalyst | Wt. g[b] | Conversion % $O_2$ | $C_4H_{10}$ | CO | $CO_2$ | $C_2$ | $C_3$ | 1-$C_4H_8$ | t-2-$C_4H_8$ | c-2-$C_4H_8$ | $C_4H_6$ | dehyd.[c] |
|---|---|---|---|---|---|---|---|---|---|---|---|---|
| MgO | 1.9[d] | 17 | 10.5 | 21.1 | 34.5 | 11.2 | 19.8 | 5.0 | 5.0 | 0 | 0 | 10.0 |
| $V_2O_5$ | 0.2[d] | 6 | 3.7 | 0 | 35 | 0 | 35 | 17 | 0 | 0 | 0 | 17 |
|  | 0.4[d] | 15 | 5.1 | 0 | 54 | 0 | 25 | 18 | 0 | 0 | 0 | 18 |
|  | 1.9[d] | — | 48.2 | 23.4 | 65.1 | 0 | 0.6 | 3.5 | 3.3 | 2.7 | 1.4 | 10.9 |
| MgO + $V_2O_5$ | 0.5 + 0.95[d] | 99 | 41 | 15.9 | 69.8 | 1.2 | 1.2 | 3.4 | 4.0 | 2.2 | 2.2 | 11.8 |
| 3V—Mg—O | 0.3 | 85 | 35.5 | 24.9 | 50.7 | 6.8 | 4.3 | 5.5 | 1.5 | 1.3 | 4.3 | 12.6 |
| 8V—Mg—O | 0.3 | 97 | 50.9 | 19.7 | 42.7 | 3.2 | 1.8 | 4.6 | 3.3 | 3.2 | 20.4 | 31.5 |
| 19V—Mg—O | 0.3 | 97 | 58.7 | 15.3 | 31.8 | 2.3 | 1.0 | 7.0 | 1.8 | 2.3 | 37.7 | 48.8 |
|  | 0.1 | 46 | 34.2 | 12.3 | 24.3 | 2.4 | 4.9 | 14.4 | 4.9 | 5.5 | 30.8 | 55.6 |
| 24V—Mg—O | 0.1 | 95 | 56.2 | 17.0 | 30.1 | 1.8 | 0.8 | 7.9 | 2.3 | 2.7 | 37.2 | 50.1 |
| 35V—Mg—O | 0.1 | 66 | 42.1 | 17.0 | 26.6 | 2.4 | 1.7 | 12.0 | 3.9 | 4.7 | 31.2 | 51.8 |
| 54V—Mg—O | 0.1 | 42 | 31.3 | 15.9 | 21.9 | 2.8 | 5.1 | 15.9 | 6.2 | 7.2 | 24.2 | 53.5 |

Footnotes to table 4:
[a]Reaction temperature 540° C., feed 4% butane and 8% $O_2$ in He.
[b]Unless noted, the catalysts were diluted with twice the weight of silica.
[c]total selectivity to form butenes and butadiene
[d]undiluted with silica

Selectivity vs. Conversion tion. This indicated the reductiion of V(V) to lower oxidation states.

TABLE 4

Effect of Conversion on the Selectivity[a]

| Catalyst | Wt. g[b] | Conversion % $O_2$ | $C_4H_{10}$ | CO | $CO_2$ | $C_2$ | $C_3$ | 1-$C_4H_8$ | t-2-$C_4H_8$ | c-2-$C_4H_8$ | $C_4H_6$ | dehyd.[c] |
|---|---|---|---|---|---|---|---|---|---|---|---|---|
| 19V—Mg—O | 0.5[d] | 98 | 59.2 | 16.5 | 36.8 | 2.8 | 0.7 | 5.8 | 1.8 | 2.1 | 33.2 | 42.9 |
|  | 0.5 | 98 | 57.3 | 15.7 | 34.2 | 2.6 | 1.1 | 6.6 | 2.1 | 2.6 | 34.9 | 46.2 |
|  | 0.3 | 97 | 58.7 | 15.3 | 31.8 | 2.3 | 1.0 | 7.0 | 1.8 | 2.3 | 37.7 | 48.8 |
|  | 0.2 | 73 | 47.2 | 14.9 | 30.8 | 2.0 | 2.0 | 9.7 | 2.8 | 3.6 | 33.5 | 49.6 |
|  | 0.1 | 46 | 34.2 | 12.4 | 24.3 | 2.4 | 4.9 | 14.4 | 4.9 | 5.5 | 30.8 | 55.6 |

Footnote
[a]Reaction temperature 540° C.; feed 4% butane, 8% $O_2$, 88% He.
[b]unless specified, the catalysts were diluted with twice the weight of $SiO_2$.
[c]total selectivity to butenes and butadiene.
[d]undiluted samples Table 4 shows the data on the effect of conversion. If the oxygen conversion was substantially less than 100%, the selectivity for butadiene increased with increasing conversion, while the total selectivity for dehydrogenation decreased. If the amount of catalyst was more than enough for complete oxygen conversion, the selectivity for butenes and butadiene decreased slightly. Presumably, in the region of the catalyst bed where there was no gaseous oxygen, the reaction products could reduce the catalyst and form carbon oxides, Indeed, in such a circumstance, the portion of the catalyst nearer the reaction outlet turned bluish gray after reaction.

Effect of Temperature

The effect of temperature was also investigated and the results are shown in Table 5. As expected, an increase in the temperature resulted in an increase in the conversion. This was achieved with only a small penalty in the selectivity for dehydrogenation. The selectivity for butadiene actually increased, while those of the butenes descreased. There was a slight increase in the selectivity for the combustion products, and the selectivity for the cracked products remained small.

TABLE 5

Effect of Temperature in Butane Oxidation over V—Mg—O[a]

| Catalyst[b] | T °C. | Conversion % $O_2$ | $C_4H_{10}$ | CO | $CO_2$ | $C_2$ | $C_3$ | 1-$C_4H_8$ | t-2-$C_4H_8$ | c-2-$C_4H_8$ | $C_4H_6$ | dehyd.[c] |
|---|---|---|---|---|---|---|---|---|---|---|---|---|
| 19V—Mg—O | 510 | 23 | 18.7 | 14.3 | 19.8 | 1.2 | 5.5 | 18.0 | 7.4 | 8.1 | 21.7 | 55.2 |
|  | 540 | 46 | 34.2 | 12.3 | 24.3 | 2.4 | 4.9 | 14.4 | 4.9 | 5.5 | 30.8 | 55.6 |
|  | 570 | 83 | 53.7 | 15.3 | 26.6 | 3.1 | 3.7 | 8.9 | 2.6 | 3 | 36.1 | 50.6 |
|  | 600 | 98 | 63.3 | 15.8 | 27.0 | 4.1 | 1.5 | 7.6 | 2.1 | 2.6 | 38.7 | 51.0 |
| 24V—Mg—O | 480 | 27 | 10.9 | 4.9 | 30.8 | 0 | 4.9 | 11.0 | 8.5 | 8.5 | 25.8 | 53.8 |
|  | 510 | 64 | 40.5 | 15.8 | 29.7 | 1.2 | 0.8 | 11.4 | 3.6 | 4.5 | 32.9 | 52.4 |
|  | 540 | 95 | 56.2 | 17.0 | 30.1 | 1.8 | 0.8 | 7.9 | 2.3 | 2.7 | 37.2 | 50.1 |
| 35V—Mg—O | 510 | 31 | 23.0 | 14.1 | 22.7 | 2.0 | 4.5 | 17.1 | 7.1 | 8.0 | 23.1 | 55.3 |
|  | 540 | 66 | 42.1 | 17.0 | 26.6 | 2.4 | 1.7 | 12.0 | 3.9 | 4.7 | 31.2 | 51.8 |
|  | 570 | 99 | 61.7 | 18.5 | 27.5 | 3.2 | 1.3 | 7.1 | 2.1 | 2.5 | 37.6 | 49.3 |
| 54V—Mg—O | 510 | 21 | 17.6 | 14.4 | 21.4 | 2.8 | 7.0 | 18.7 | 8.4 | 9.3 | 16.8 | 53.2 |
|  | 540 | 42 | 31.3 | 15.9 | 21.9 | 2.8 | 5.1 | 15.9 | 6.2 | 7.2 | 24.2 | 53.5 |

Footnotes
[a]Feed: 4% butane, 8% $O_2$, 88% He.
[b]0.1 g catalyst diluted with 0.2 g silica.
[c]total selectivity for butenes and butadiene.

Effect of Oxygen to Butane Ratio

Table 6 shows the effect of the oxygen-to-butane ratio in the feed. This ratio was varied by changing the partial pressure of oxygen while keeping the partial pressure of butane fixed. With a decreasing oxygen-to-butane ratio, the butane conversion decreased whereas the oxygen conversion increased. The total selectivity for dehydrogenation also increased mostly due to the increase in butenes. There might be a slight but not significant increase in the cracked products.

TABLE 6

Effect of Feed Composition in Butane Oxidation on V—Mg—O[a]

| Catalyst[b] | Feed $C_4H_{10}/O_2$ | Conversion % $O_2$ | $C_4H_{10}$ | CO | $CO_2$ | $C_2$ | $C_3$ | Selectivity % ($C_4$ basis) 1-$C_4H_8$ | t-2-$C_4H_8$ | c-2-$C_4H_8$ | $C_4H_6$ | dehyd. |
|---|---|---|---|---|---|---|---|---|---|---|---|---|
| 19V—Mg—O | 4/8 | 73 | 47.2 | 14.9 | 30.8 | 2 | 2 | 9.7 | 2.8 | 3.6 | 33.5 | 49.6 |
| | 4/6 | 83 | 42.7 | 13.2 | 27.5 | 1.9 | 3.0 | 11.4 | 3.3 | 4.2 | 35.2 | 54.1 |
| | 4/4 | 95 | 28.5 | 10.2 | 11.5 | 1.5 | 4.5 | 16.2 | 5.6 | 6.9 | 31.7 | 60.4 |

Footnotes
[a]Reaction temperature 540° C., feed: 4% butane, varying $O_2$, balance He.
[b]0.2 g catalyst diluted with 0.4 g silica.

EXAMPLE II

Two catalysts, 24 V-Mg-O and 40 V-Mg-O, prepared in the same way as those described in Example I, were used in the oxidation of propane. The feed mixture consisted of 4% propane, 8% oxygen, and the balance He. About 0.1 to 0.2 g of catalyst diluted with silica gel was used in this reaction study. High conversions were observed at a temperature of 500° C. Some typical data are shown in Table 7.

TABLE 7

Conversion and Selectivity in Propane Oxidative Dehydrogenation over V—Mg—O Catalyst[a]

| Temp C. | Catalyst | Conversion % $C_3H_8$ | $O_2$ | CO | $CO_2$ | Selectivity % ($C_3$ basis) $C_2$ | $C_3H_6$ |
|---|---|---|---|---|---|---|---|
| 500 | 24V—Mg—O | 11.9 | 16.3 | 13.3 | 24.6 | 0 | 62.1 |
| | | 18.6 | 28.5 | 16.3 | 30.8 | 0 | 52.9 |
| | | 24.1 | 37.5 | 18.3 | 40.6 | 0 | 41.1 |
| | 40V—Mg—O | 8.4 | 13.6 | 13.7 | 24.0 | 0 | 62.3 |
| | | 15.6 | 20.6 | 16.6 | 30.4 | 0 | 53.0 |
| | | 23.5 | 38.0 | 19.7 | 37.6 | 0 | 42.7 |
| 540 | 24V—Mg—O | 13.4 | 20.5 | 13.2 | 23.6 | 0 | 63.2 |
| | | 20.8 | 30.1 | 16.2 | 30.7 | 0 | 53.1 |
| | | 28.9 | 46.6 | 19.0 | 37.2 | 1.4 | 42.4 |
| | 40V—Mg—O | 13.9 | 17.8 | 15.5 | 23.5 | 0 | 61.0 |
| | | 25.0 | 33.4 | 19.8 | 30.2 | 1.6 | 48.4 |

[a]Feed condition: 4% propane, 8% oxygen, in He.

Propane dehydrogenation can be carried out also with other propane to oxygen ratios. In an experiment using 0.1 g of the 24 V-Mg-O catalyst at 540° C. and a feed containing 4% propane, the oxygen content in the feed was varied from 4 to 8%. The propane conversion and the propene selectivity were found to be 22.8 and 52.8%, 25.4 and 49.9%, and 32.9 and 42.9%, respectively, for the propane/oxygen ratios of 1/1, 1/1.5 and 1/2.

EXAMPLE III

Zinc orthovanadate, $Zn_3V_2O_8$ was prepared by adding a stoichiometric amount of 0.3M solution of ammonium vanadate to ZnO. Thus 5 g of ZnO was mixed with 136.5 ml of 0.3 M solution of $NH_4VO_3$. The suspension was evaporated with stirring to dryness. The powder was further dried in an oven at 70° C. overnight, and then calcined at 720° C. for 6 h. The resulting solid weighed 8.7 g. It was lightly crushed before being used as a catalyst. It showed an X-ray diffraction pattern of only zinc orthovanadate.

2 g of the catalyst was used in the oxidation of propane in the same reaction system as in Example I. The feed was 4% propane, 8% oxygen, and the balance He at a total flow rate of about 100 ml/min. The conversion and the selectivity obtained are shown in Table 8.

TABLE 8

Conversion and Selectivity in Propane Oxidation over Zinc Orthovanadate

| Experiment | 1 | 2 |
|---|---|---|
| Temp. °C. | 558 | 590 |
| Propane conversion % | 23.4 | 40.9 |
| oxygen conversion % | 13.0 | 16.8 |
| Selectivity % | | |
| $C_3H_6$ | 69.3 | 51.0 |
| $C_2H_4$ | 17.1 | 24.7 |
| $C_2H_6$ | trace | trace |
| $CH_4$ | 4.0 | 8.7 |
| CO | 3.5 | 9.0 |
| $CO_2$ | 6.1 | 6.6 |

EXAMPLE IV 1 g of magnesium metavanadate, $MgV_2O_6$, prepared by calcining a stoichiometric mixture of $V_2O_5$ and MgO was used in the oxidation of propane. The feed contained 4% propane, 8% oxygen in He. At 610° C., the propane conversion was 11%, and the selectivity was 71% for propene, 26% for $C_2$ products, and 3% for $CO_2$.

EXAMPLE V

The catalyst, zinc orthovanadate, used in Example III was used in the oxidation of butane at 580° C. using a butane:$O_2$:He of 4:8:88. At 23.6% conversion of butane, a product was obtained that contained 23.2% butadiene, 15.9% 1-butene, 2.7% cis-2-butene, 5.6% trans-2-butene, 6.8% propene, 9.9% ethene, 11.3% methane, 23.9% $CO_2$, and trace amounts of propane and CO.

EXAMPLE VI

Mixtures of MgO and ZnO were prepared by adding an ammonium carbonate solution to a solution containing a mixture of zinc and magnesium nitrate. The precipitate was filtered and dried in an oven at 80° C. overnight. The dried solid was then calcined at 700° C. X-ray diffraction showed that the solid was a mixture of MgO and ZnO.

An appropriate amount of this solid was mixed with a 0.3 M solution of ammonium vanadate to yield a final solid containing the ratio of V to MgO and ZnO equivalent to 2 wt % $V_2O_5$. The suspension was dried and calcined at 625° C. The infrared spectra of the final solid showed the absence of $V_2O_5$, which had a characteristic band at 1022 $cm^{-1}$.

These mixtures were found to catalyze the oxidative dehydrogenation of butane under conditions similar to that used in Example I. Table 9 shows some typical results:

TABLE 9

Conversion and Selectivity in Oxidative Dehydrogenation of Butane on V—Mg—Zn—O Catalysts at 540° C., butane/$O_2$/He = 4/8/88

| Catalyst Mg:Zn | wt. used | butane conversion % | Selectivity % $C_4H_8$ | $C_4H_6$ | total $C_4$ dehydrogenation |
|---|---|---|---|---|---|
| 1:5 | 1.0 g | 28.9 | 21.3 | 30.2 | 51.5 |
| 1:3 | 1.76 g | 14.8 | 24.9 | 33.0 | 57.9 |
| 1:1 | 1.6 g | 19.5 | 19.3 | 30.6 | 49.9 |
| 3:1 | 1.8 g | 53.5 | 10.8 | 29.8 | 40.6 |

EXAMPLE VII

The catalyst 40 V-Mg-O was used in the oxidation of 2methylpropane at 540° C., with a feed containing 4% 2-methylpropane, 8% $O_2$, and 88% He. At 35% conversion of the alkane, 2- methylpropene was produced with a selectivity of 22.1%.

REFERENCES

Bretton et al., (1952) Ind. Eng. Chem. 44:594
Clark et al., (1976), J. Solid State Chem., 16:429
Doroshenko et al. (1982), Prik. Khim. 55, 80
Hanuza et al. (1985), J. Mol. Catal. 29, 109
Hodnett, et al., (1985), Catal. Rev. 27, 373
Inomata, et al. (1981), J. Phys. Chem., 85:2372
Iwamoto, et al., (1985), App. Catal. 16:153
Kristallov et al., (1984), Russ. J. Inorg. Chem., 29:990
Mori et al. (1986), Soc. Faraday Trans. I, 82:13
Mori et al. (1982), Appl. Catal. 6:209
Moser et al. (1985), J. Catal., 92:216
Oganowski et al. (1984), Bull. Pol. Acad. Sci. Chem. 31:129
Simakov et al. (1985), React. Kinet. Catal. Lett. 28:67
Stepanov et al., (1981), Stud. Surf. Sci. Catal. 7:1293

We claim:

1. The oxidative dehydrogenation method of selectively converting alkanes to unsaturated hydrocarbons while suppressing the formation of oxygenate hydrocarbon by-products, comprising:
   (a) providing a catalyst bed composed essentially of one or a plurality of metal vanadate compounds selected from the group of vanadate compounds represented by the formulas $M_3(VO_4)_2$ and $MV_2O_6$ wherein M is selected from magnesium (Mg), zinc (Zn); calcium (Ca), lead (Pb), and cadmium (Cd); and
   (b) passing through said bed a vapor phase reaction mixture containing oxygen and a saturated alkane reactant containing from 2 to 8 carbons, from 0.5 to 10 moles oxygen ($O_2$) being present per mole of alkane and said mixtures being at a reaction temperature in the range from 300° to 700° C.

2. The method of claim 1 in which said vanadate compound is selected from the group consisting of $MG_3(VO_4)_2$, $Zn_3(VO_4)_2$, $MgV_2O_6$, and $ZnV_2O_6$.

3. The method of claim 1 in which said vanadate compound is magnesium orthovanadate.

4. The method of claim 1 in which said vanadate compound is zinc orthovanadate.

5. The method of claim 1 in which said vanadate compound is magnesium metavanadate.

6. The method of claim 1 in which said vanadate compound is zinc metavanadate.

7. The method of claim 1 in which said alkane reactant is ethane and said vanadate compound is zinc orthovanadate.

8. The method of claim 1 in which said alkane reactant is selected from the group consisting of propane, butane, and isobutane.

9. The method of claim 1 in which said alkane reactant is selected from the group consisting of straight and branched chain pentanes.

10. The method of claim 1 in which said alkane reactant is selected from the group consisting of straight and branched chain hexanes.

11. The method of claims 1, 2, 3, 4, 5, 6, 7, 8, 9, or 10 in which during the passage of said reaction mixture through said bed from 5 to 70% of said alkane reactant is converted to one or more unsaturated hydrocarbons with essentially no formation of oxygenate hydrocarbon by-products.

12. The oxidative dehydrogenation method of selectively converting alkanes to unsaturated hydrocarbons while suppressing the formation of oxygenate by-products, comprising:
   (a) providing a catalyst bed composed essentially of one or a plurality of metal vanadate compounds selected from the group of vanadate compounds represented by the formula $M_3(VO_4)_2$ wherein M is magnesium (Mg) or zinc (Zn); and
   (b) passing through said bed a vapor phase reaction mixture containing oxygen and a saturated alkane hydrocarbon reactant containing from 3 to 6 carbons, from 0.5 to 4 moles oxygen ($O_2$) being present per mole of alkane and said mixtures being at a temperature of from 400° to 600° C.

13. The oxidative dehydrogenation method of selectively converting alkanes to unsaturated hydrocarbons while suppressing the formation of oxygenated by-products, comprising:
   (a) providing a catalyst bed essentially of one or a plurality of metal vanadate compounds selected from the group of vanadate compounds represented by the formula $MV_2O_6$ wherein M is magnesium (Mg) or zinc (Zn); and
   (b) passing through said bed a vapor phase reaction mixture containing oxygen and a saturated alkane hydrocarbon reactant containing from 3 to 6 carbons, from 0.5 to 4 moles oxygen ($O_2$) being present per mole of alkane and said mixtures being at a temperature of from 400° to 600° C.

14. The method of claim 12 in which said vanadate compound is selected from the group consisting of $MG_3(VO_4)_2$ and $Zn_3(VO_4)_2$.

15. The method of claim 13 in which said vanadate compound is selected from the group consisting of $MgV_2O_6$ and $ZnV_2O_6$.

16. The method of claim 12 in which said vanadate compound is magnesium orthovanadate.

17. The method of claim 12 in which said vanadate compound is zinc orthovanadate.

18. The method of claim 13 in which said vanadate compound is magnesium metavanadate.

19. The method of claim 13 in which said vanadate compound is zinc metavanadate.

20. The method of claim 12 or claim 13 in which said alkane reactant is propane.

21. The method of claim 12 or claim 13 in which said alkane reactant is selected from the group consisting of butane and isobutane.

22. The method of claim 12 or claim 13 in which said alkane reactant is selected from the group consisting of straight and branched chain pentanes.

23. The method of claim 12 or claim 13 in which said alkane reactant is selected from the group consisting of straight and branched chain hexanes.

24. The method of claims 12 and 13 in which during the passage of said reactant mixture through bed, from 5 to 60% of said alkane reactant is converted to one or more unsaturated hydrocarbons with essentially no formation of oxygenate hydrocarbon by-products.

* * * * *

UNITED STATES PATENT AND TRADEMARK OFFICE
CERTIFICATE OF CORRECTION

PATENT NO. : 4,777,319
DATED : October 11, 1988
INVENTOR(S) : Harold H. Kung & Mohamed Ali Chaar It is certified that error appears in the above-identified patent and that said Letters Patent is hereby corrected as shown below:

In column 1, line 47, correct "$MG_3$" to --$Mg_3$--.

In column 11, line 63, correct "$MG_3$" to --$Mg_3$--.

In column 12, line 55, correct "$MG_3$" to --$Mg_3$--.

Signed and Sealed this

Twenty-first Day of February, 1989

Attest:

DONALD J. QUIGG

*Attesting Officer*   *Commissioner of Patents and Trademarks*